United States Patent
Fenton, Jr.

(10) Patent No.: US 6,488,196 B1
(45) Date of Patent: Dec. 3, 2002

(54) SURGICAL STAPLER AND METHOD OF APPLYING PLASTIC STAPLES TO BODY TISSUE

(75) Inventor: Paul V. Fenton, Jr., Marblehead, MA (US)

(73) Assignee: Axya Medical, Inc., Beverly, MA (US)

( * ) Notice: Subject to any disclaimer, the term of this patent is extended or adjusted under 35 U.S.C. 154(b) by 50 days.

(21) Appl. No.: 09/608,299

(22) Filed: Jun. 30, 2000

Related U.S. Application Data

(60) Provisional application No. 60/141,740, filed on Jun. 30, 1999.

(51) Int. Cl.[7] .............................................. A61B 17/068
(52) U.S. Cl. .................. 227/175.1; 227/19; 227/176.1; 227/902; 606/32; 606/42; 606/219
(58) Field of Search ........................... 227/175.1, 176.1, 227/178.1, 180.1, 19, 901, 902; 606/40, 32, 52, 46

(56) References Cited

U.S. PATENT DOCUMENTS

| | | | |
|---|---|---|---|
| 3,757,629 A | | 9/1973 | Schneider ....................... 85/49 |
| 5,324,307 A | * | 6/1994 | Jarrett et al. ................. 606/219 |
| 5,452,837 A | | 9/1995 | Williamson, IV et al. .. 227/176 |
| 5,582,611 A | * | 12/1996 | Tsuruta et al. ................. 606/46 |
| 5,662,258 A | * | 9/1997 | Knodel et al. ........... 227/175.1 |
| 5,807,393 A | * | 9/1998 | Williamson, IV et al. .... 606/32 |
| 5,833,690 A | * | 11/1998 | Yates et al. .................... 606/52 |
| 6,004,335 A | | 12/1999 | Vaitekunas et al. ......... 606/169 |
| 6,024,741 A | * | 2/2000 | Williamson, IV et al. .... 606/40 |

* cited by examiner

*Primary Examiner*—Scott A. Smith
(74) *Attorney, Agent, or Firm*—McDermott, Will & Emery

(57) ABSTRACT

A surgical stapler utilizing plastic staples and ultrasonic welding to secure the staples in body tissue. The stapler includes a pair of jaws movable between open and closed positions, a handle and trigger assembly for controlling operation of the jaws, and an elongated tubular structure connecting the handle and trigger assembly to the jaws. The stapler also includes an ejection assembly for ejecting at least one staple from one of the jaws against the other of the jaws. An anvil and a horn are positioned in the other of the jaws and are arranged to receive ends of the ejected staple such that the ends overlap between the anvil and the horn. The horn is for melting and bonding at least a portion of the overlapping ends of the staple upon being energized by a predetermined form of energy, and one of the anvil and the horn is movable from within the bonded staple to allow the jaws to be moved to an open position.

14 Claims, 5 Drawing Sheets

SURGICAL STAPLER AND METHOD OF APPLYING PLASTIC STAPLES TO BODY TISSUE

CROSS REFERENCE TO RELATED APPLICATIONS

This application is a continuation of provisional U.S. patent application Ser. No. 60/141,740, filed Jun. 30, 1999, the disclosure of which is hereby incorporated by reference into the present application.

FIELD OF DISCLOSURE

The present application, or disclosure, relates to a surgical stapler and methods of applying surgical staples to body tissue. More particularly, the present disclosure relates to surgical staplers utilizing plastic staples, and methods of applying plastic surgical staples to body tissue.

BACKGROUND OF THE DISCLOSURE

There is an increasing use of surgical staplers to unite, close or secure body tissue such as intestine, lung, stomach, and esophagus. Stapling tissue in most instances produces less scar tissue formation, requires less time and simplifies previously difficult surgical procedures when compared with traditional suturing methods. Surgical staplers of the type used in these procedures function generally by clamping body tissue between two opposed jaws of the stapler to a desired thickness, and firing staples through the tissue to unite, close or secure the tissue.

Surgical staplers can be provided in many forms, such as a single staple application-type stapler, a circular stapler, and a linear stapler. Each of these types of surgical staplers include a pair of clamps or jaws movable from an open to a closed position to clamp body tissue there between. The staplers include ejection means for ejecting at least one staple from one of the clamps, through the clamped tissue and towards the other of the clamps. Barbed ends of the staple are bent over against the other of the clamps to secure the staple in the tissue.

Circular and linear type staplers are typically designed to apply multiple, concentric or parallel rows of staples. These types of staplers can additionally be provided with a movable knife between pairs of staggered staple rows, in order to make incisions in the tissue between the stapled portions of the tissue.

Usually, surgical staples are made of a metal that is bio-compatible, but not bio-absorbable. The metal staples, therefore, must eventually be removed by another device such as a staple extractor, which is not only time consuming but can cause discomfort and pain to the patient. Plastic staples, in contrast, can be made bio-absorbable. In addition, plastic staples are often more bio-compatible than metal staples, and often do not effect medical diagnostic techniques, such as magnetic resonance imaging, computer tomography scanning, and ultrasound detection, to the same degree as metal staples. What is desired, accordingly, are surgical staplers utilizing plastic staples, and methods of applying plastic surgical staples to body tissue.

SUMMARY OF DISCLOSURE

In response, the present disclosure provides a surgical stapler utilizing plastic staples, and ultrasonic welding to secure the staples in body tissue. The stapler includes a pair of jaws movable between open and closed positions, a handle and trigger assembly for controlling operation of the jaws, and an elongated tubular structure connecting the handle and trigger assembly to the jaws. The stapler also includes an ejection assembly for ejecting at least one staple from one of the jaws against the other of the jaws. An anvil and a horn are positioned in the other of the jaws and are arranged to receive ends of the ejected staple such that the ends overlap between the anvil and the horn. The horn is for melting and bonding at least a portion of the overlapping ends of the staple upon being energized by a predetermined form of energy, and one of the anvil and the horn is movable from within the bonded staple to allow the jaws to be moved to an open position.

The present disclosure also provides another surgical stapler utilizing staples. The stapler is for ejecting at least one staple of resilient thermoplastic material having a base member and two legs extending from the base member to sharp ends, wherein the legs include overlapping distal portions for engaging body tissue. The stapler includes a pair of jaws movable between open and closed positions, an ejection assembly for ejecting a staple from one of the jaws against the other of the jaws, and posts for holding normally overlapping distal portions of legs of the staple generally parallel until the staple is ejected from the stapler.

Methods of stapling body tissue are also provided by the present disclosure. These and other features of the unique surgical staplers and surgical stapling methods of the subject application will become more readily apparent to those skilled in the art from a review of the following detailed description and the attached drawings.

BRIEF DESCRIPTION OF THE DRAWINGS

Like features in the figures are labeled with like reference numerals.

DETAILED DESCRIPTION OF THE DISCLOSURE

Figure 1:
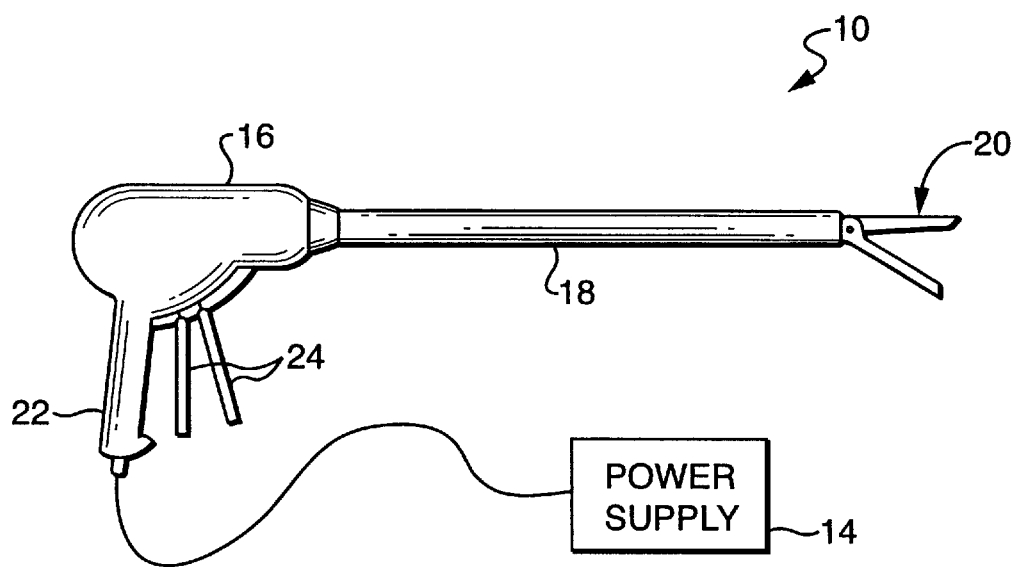
FIG. 1 is a side elevation view of a surgical stapler constructed in accordance with the present disclosure.

Referring to FIG. 1, there is shown a surgical stapler 10 constructed in accordance with the present disclosure. The unique stapler 10 utilizes plastic staples 12 and ultrasonic welding to secure the staples in body tissue. As shown in FIG. 1, the stapler 10 is connected to a power supply 14, comprising part of an ultrasonic welding system of the stapler.

The stapler 10 includes a body 16 and an elongated tubular structure 18 extending from the body and having a proximal end attached to the body and a distal end furthest from the body. Jaws 20 extend from the distal end of the tubular structure 18, and a handle 22 and triggers 24 extend from the body 16 and are operatively connected to the jaws 20 to remotely control the jaws and components contained within the jaws. Although not shown here in detail, the opening and closing movement of the jaws 20 is controlled by one of the triggers 24 through the elongated tubular structure 18 of the stapler 10. Triggering mechanisms for controlling jaws at a distal end of an elongated tubular member can take many forms and are, in general, known to those skilled in the art of surgical staplers. Triggering mechanisms, therefore, are not described here in detail.

Figure 2:
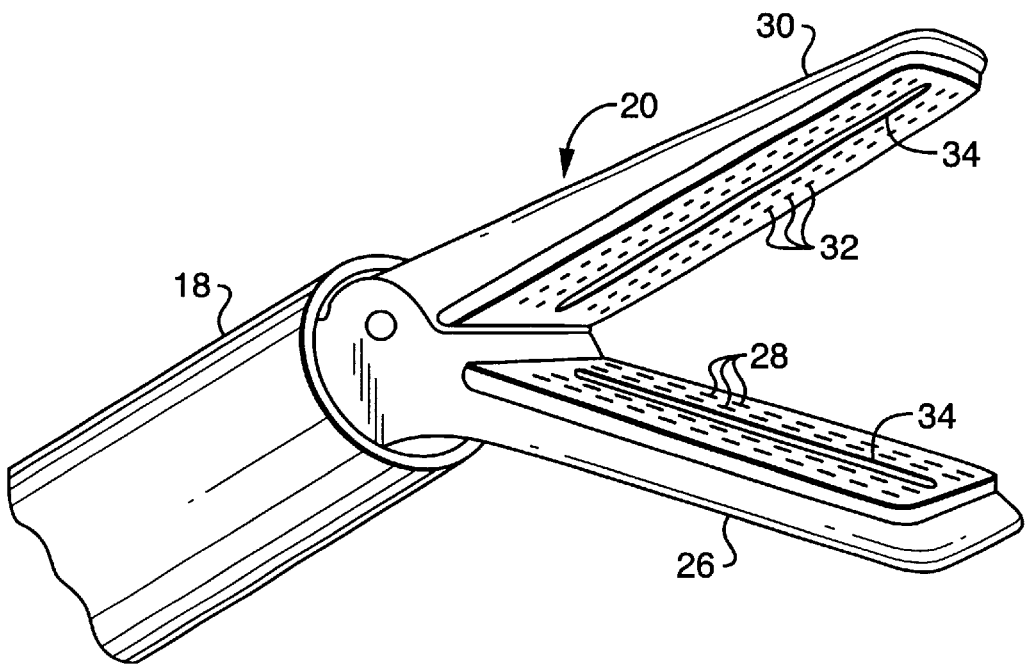
FIG. 2 is an enlarged side perspective view of jaws of the surgical stapler of FIG. 1, shown in an open position.

Referring also to FIG. 2, the particular embodiment of the stapler 10 according to the present disclosure is a linear type stapler having pivotally joined jaws 20. It should be understood however, that the unique features of the present disclosure can also be applied in other types of surgical staplers, such as a circular type surgical stapler. In general, the linear type stapler 10 is for providing parallel, but staggered rows of staples 12 for uniting, closing or securing body tissue, such as intestine, lung, stomach, and esophagus. In particular, the stapler 10 provides parallel pairs of staggered rows of staples 12, and a lower jaw 26 of the stapler includes slots 28 for ejecting staples, while an upper jaw 30 of the stapler includes recesses 32 for receiving and forming ends of the ejected staples. The jaws 20 can also include opposing longitudinal knife channels 34 and a cutting blade (not shown) for travelling along the channels to provide an incision in the body tissue between the double rows of staples. The staples 12 reduce or prevent bleeding from the surrounding tissue due to the incision.

Figure 3:
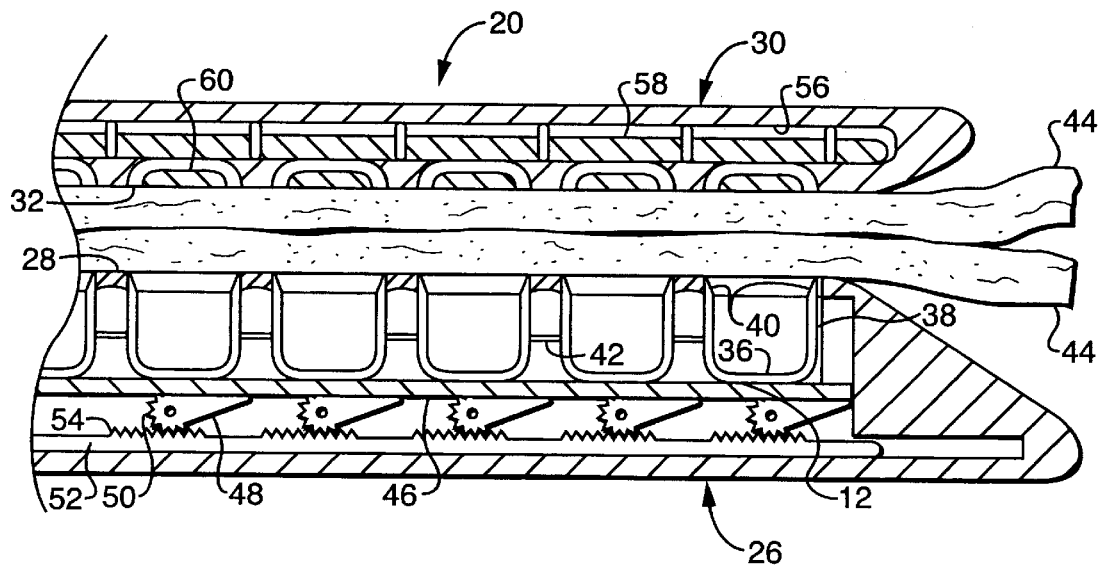
FIG. 3 is a further enlarged side sectional view of a portion of the jaws of the surgical stapler of FIG. 1, showing the jaws in a closed position clamping two layers of body tissue to be joined.
Figure 4:
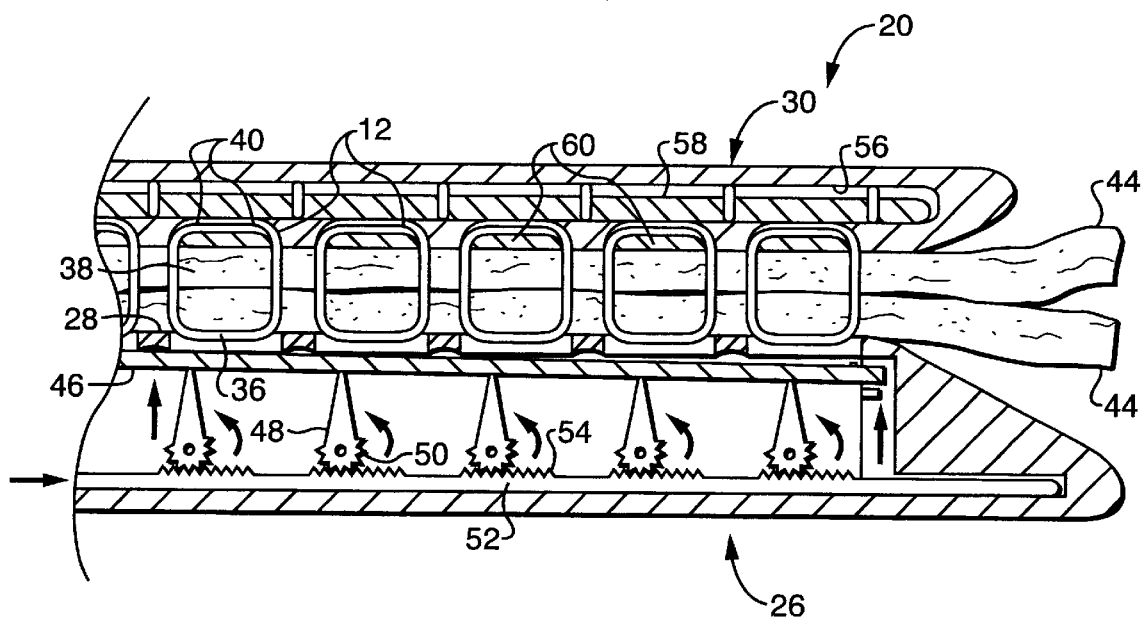
FIG. 4 is the side sectional view of the portion of the jaws of the surgical stapler of FIG. 1, showing the jaws in a closed position driving staples through the two layers of body tissue.

As shown in FIGS. 3 and 4, a plurality of surgical staples 12 are received in the lower jaw 26 of the stapler 10 for ejection through the slots 28 of the lower jaw 26. Each staple 12 comprises a single piece of a bio-compatible, resilient thermoplastic material having a base member 36 and two substantially parallel legs 38 extending perpendicular from the base member to sharp ends 40 for allowing the legs to pierce body tissue. In some cases, the staples 12 may be made from a bio-compatible, resilient thermoplastic material that is also bio-absorbable. As shown, the staples 12 extend longitudinally within the lower jaw 26 and are formed together with removable tangs 42 between each staple.

The lower jaw 26 includes an ejector system for ejecting the staples 12 from the lower jaw, through layers of body tissue 44 and against the upper jaw 30. In particular, the system includes a platform 46 for ejecting the staples 12 upon being moved towards the upper jaw 30, cams 48 for moving the platform towards the upper jaw upon being rotated, and an ejection bar 52 for rotating the cams upon being longitudinally moved within the lower jaw 26. As shown in FIGS. 3 and 4, the ejection bar 52 has teeth 54 on a top surface thereof that engage teeth 50 on the rotatable cams 48, such that as the ejection bar is longitudinally moved towards a distal end of the lower jaw 26, the cams are rotated counter-clockwise to raise the staple ejection platform 46. The ejection bar 52 is longitudinally moved by one of the triggers on the proximal end of the elongated tubular member 18 of the stapler 10.

The upper jaw 30 includes longitudinal chambers 56, and the plurality of recesses 32 for receiving and forming the ends 40 of the ejected staples 12 communicate with the chambers. The longitudinal chambers 56 receive elongated ultrasonic horns 58, while the recesses 32 receive ultrasonic anvils 60. The anvils 60 and the walls of the recesses 32 receive and guide the ends 40 of the ejected staples 12, such that the ends overlap between the anvil 60 and the horn 58 after passing through the layers of body tissue 44, as shown in FIG. 4.

Figure 5:
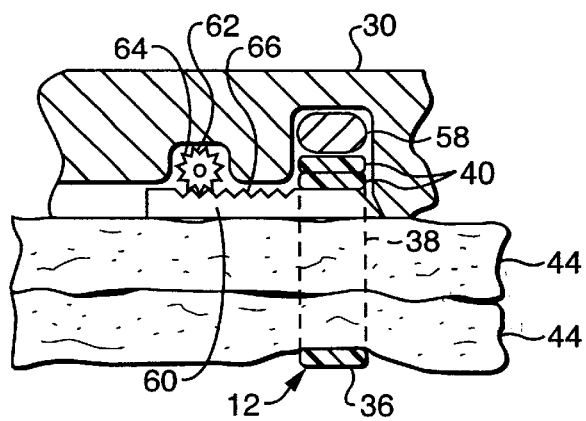
FIG. 5 is a further enlarged end sectional view of an upper jaw of the surgical stapler of FIG. 1 and the two layers of body tissue, showing two ends of one of the driven staples between an ultrasonic horn and anvil of the upper jaw.
Figure 6:
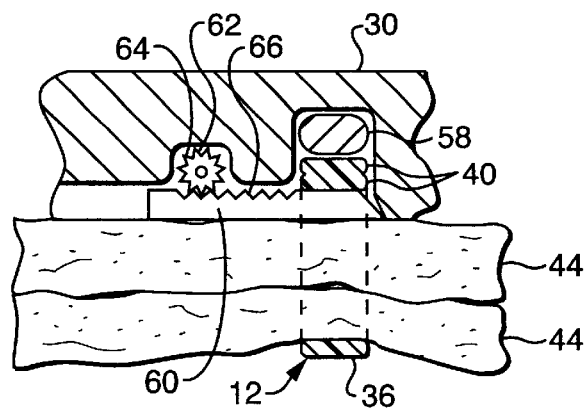
FIG. 6 is the end sectional view of the upper jaw of the surgical stapler of FIG. 1 and the two layers of body tissue, showing the two ends of the driven staple after being ultrasonically bonded between the horn and the anvil of the upper jaw to join the layers of tissue.

The ultrasonic horns 58 melt and bond at least a portion of the overlapping ends 40 of the staples 12 upon being energized by ultrasonic energy. Although not shown here, the system for providing ultrasonic energy to the horns 58 includes, for example, a power supply that takes line power at 50/60 cycles and changes it to high ultrasonic frequency of 20,000 cycles per second or higher, a converter or transducer that contains piezoelectric crystals that change the incoming high frequency electrical signal to mechanical vibration of the same frequency, and a booster that transmits the vibration energy and increases its amplitude. The horns 58 mounted longitudinally within the upper jaw 30 deliver the vibration energy by contact with the staples 12 to be bonded, and the plurality of anvils 60 support the staples 12 during bonding. FIGS. 5 and 6 show overlapping ends 40 of one of the staples 12 before and after being ultrasonically welded, respectively, between the horn 58 and the anvil 60. For purposes of illustration, the ends 40 of the staple 12 are shown in FIG. 6 to have completely melted and bonded into a single thickness. However, it should be appreciated that the stapler 10 can be adapted to simply produce a bonded region between the contacting surfaces of the overlapping ends 40.

Figure 7:
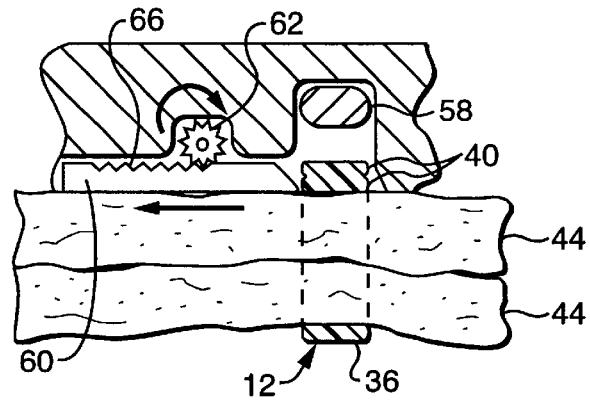
FIG. 7 is the end sectional view of the upper jaw of the surgical stapler of FIG. 1 and the two layers of body tissue, showing the anvil being withdrawn from between the bonded staple and the joined layers of tissue.
Figure 8:
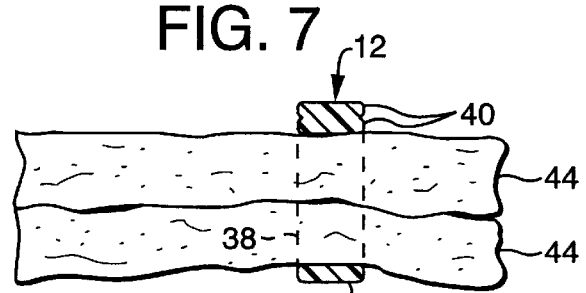
FIG. 8 is an end sectional view of the bonded staple and the joined layers of tissue after removal of the surgical stapler of FIG. 1.
Figure 9:
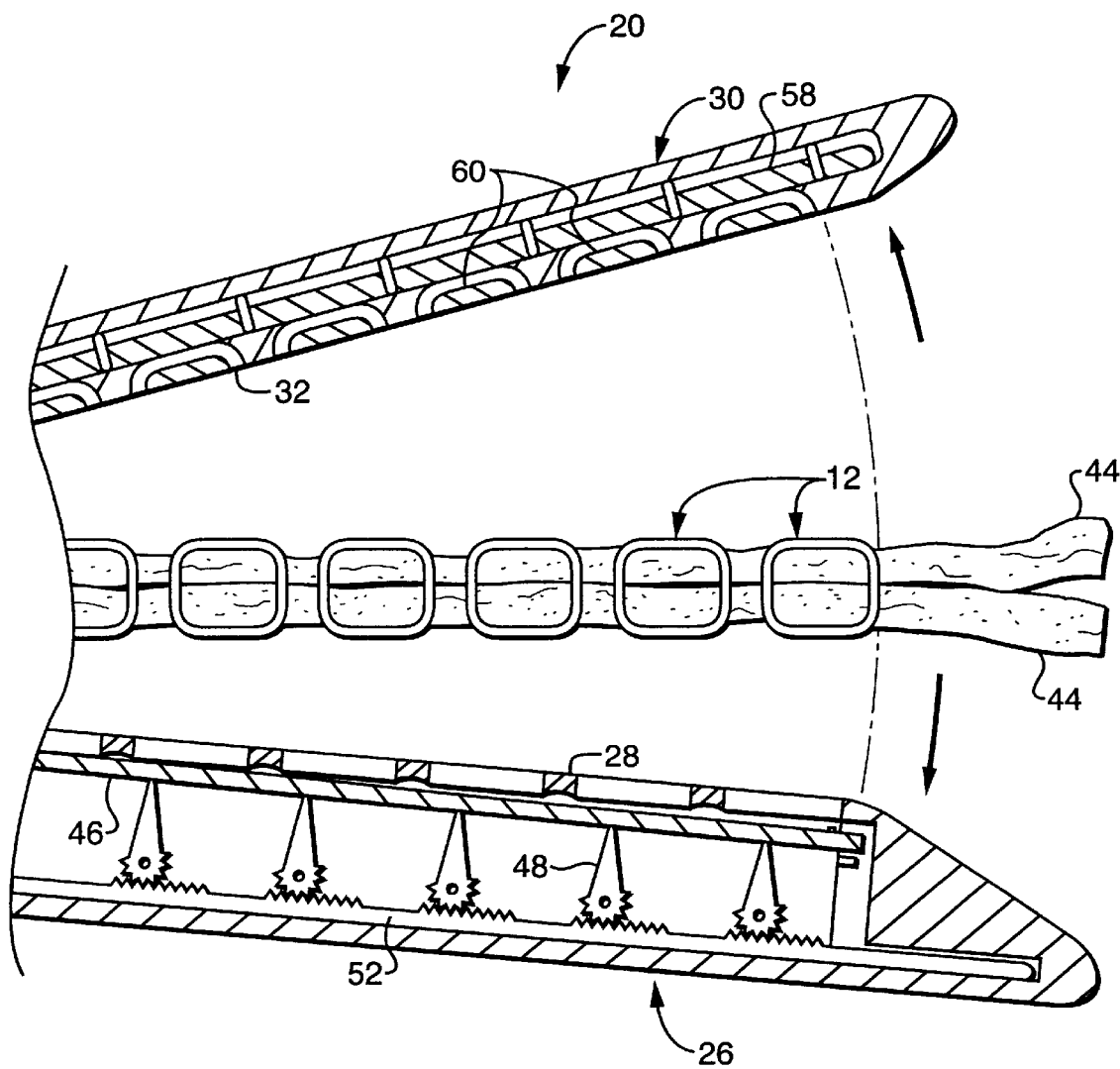
FIG. 9 is the side sectional view of the jaws of the surgical stapler of FIG. 1, showing the jaws being opened to leave the bonded staples in the joined layers of body tissue.

Once the ends 40 of the staples 12 are bonded, the anvils 60 are moved from between the bonded staple and the body tissue 44, as shown in FIG. 7, to allow the jaws 20 to be opened, as shown in FIG. 9. FIG. 8 shows one of the bonded staples 12 securing the two layers of body tissue 44 after removal of the stapler.

Referring to FIGS. 5 through 7, preferably each of the anvils 60 are moved in a lateral direction with respect to the jaws 20 and parallel with a top surface of the body tissue 44. In particular, the upper jaw 30 includes rotatable longitudinal shafts 62 having teeth 64 that mesh with teeth 66 on a top surface of the anvils 60, so that rotation of the shafts 62 causes the anvils 60 to move from between the bonded staples 12 and the body tissue 44, as shown best in FIG. 7.

As acceptable alternatives, the anvils 60 could be adapted to pivot from between the staples 12 and the tissue 44 as the jaws 20 are opened. In addition, the separate anvils 60 of each row of staples 12 can be provided as part of a unitary, elongated, anvil plate that is movable with respect to the recesses 32 of the upper jaw 30. Also, it should be understood that while the illustrated stapler 10 has anvils 60 that are moved to allow the jaws 20 to be opened, the stapler 10 can alternatively be provided with moveable horns. Many variations in the ultrasonic welding system of the presently disclosed surgical stapler 10 can be made without departing from the spirit and scope of the present disclosure.

Figure 10:
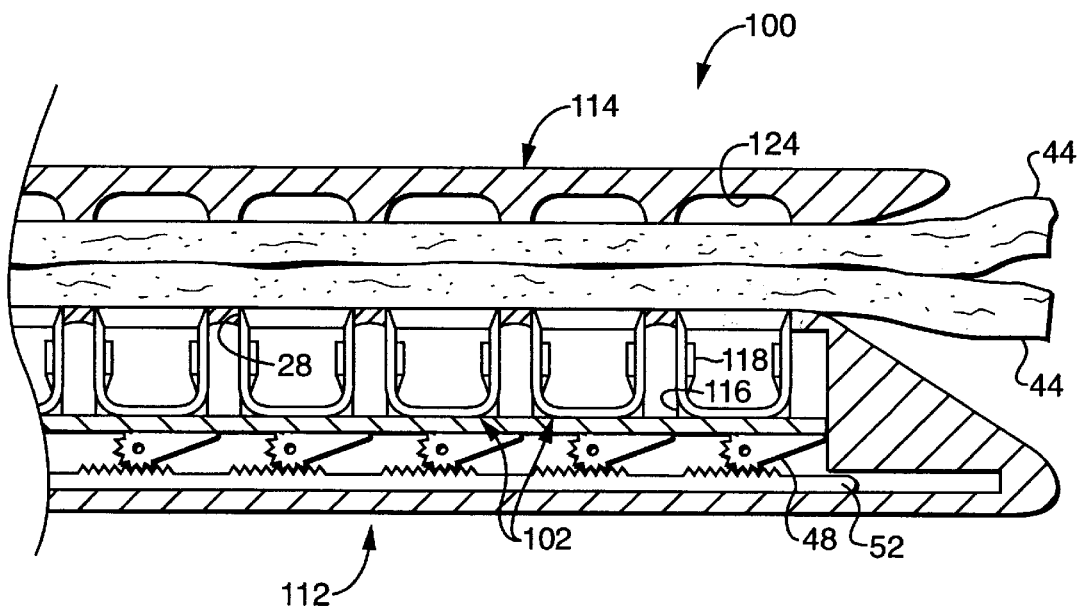
FIG. 10 is a side sectional view of jaws of another surgical stapler constructed in accordance with the present disclosure, showing the jaws in a closed position clamping two layers of body tissue to be joined.
Figure 13:
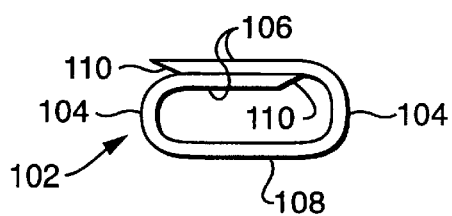
FIG. 13 is a side elevational view of the staple of the surgical stapler of FIG. 10, shown before being mounted in the stapler.
Figure 14:
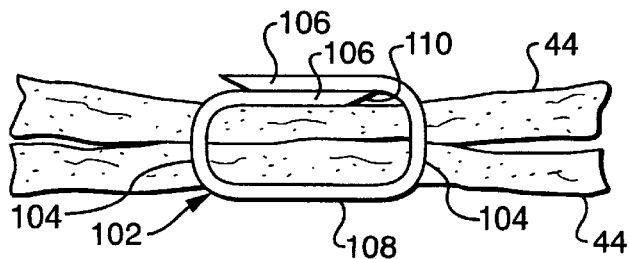
FIG. 14 is a side elevational view of the staple of the surgical stapler of FIG. 10, shown after being driven through the two layers of body tissue by the stapler to join the layers of tissue.

Referring now to FIG. 10, another surgical stapler 100 constructed in accordance with the present disclosure is shown. The stapler 100 is similar to the stapler 10 of FIG. 1, except that the stapler 100 of FIG. 10 does not include an ultrasonic welding system for bonding staples. Instead, staples 102 of the stapler of FIG. 10 are provided with resilient legs 104 having distal portions 106 which are normally bent towards each other, such that the distal portions of the legs overlap, as shown in FIG. 13. When the staples 102 are inserted through body tissue 44 the overlapping leg portions 106 of the staples act to secure the staple to the body tissue, as shown in FIG. 14. The stapler 100 is designed to hold the distal portions 106 of the legs 104 of the staples 102 parallel, and to eject the staples through the layers of tissue 44 so that the distal portions 106 return to their overlapped positions and secure the tissue without ultrasonic welding.

The staples 102 of the stapler 100 of FIG. 10, are single piece surgical staples having a base member 108, and the two legs 104 extend perpendicular from the base member. In addition to the bent-over distal portions 106, the legs have sharp ends 110 to allow the legs to pierce body tissue. The staples 102 are made from bio-compatible, resilient thermoplastic material that tends to return to its normal position after being displaced therefrom and is said to have an "elastic memory." In some cases, the staples 102 may be made from a bio-compatible, resilient thermoplastic material that is also bio-absorbable.

It should be understood, that the staples 102 can alternatively be provided with legs having distal portions that, in their normal released positions, bend outwardly away from each other, instead of overlapping. The staples 102 can also be provided with barbs extending outwardly therefrom for catching on the body tissue, to allow the staples to further secure the tissue.

A lower jaw 112 of the stapler 100 includes an ejector system for ejecting the staples 102 from the lower jaw, through the layers of body tissue 44 and against an upper jaw 114. The ejecting system is similar to the ejecting system of FIGS. 3 and 4, but includes staple mounts 116 mounted to the platform 46 for holding the distal portions 106 of the legs 104 of the staples 102 parallel before and during the driving or insertion of the staples into body tissue. The staple mounts 116 also allow the distal portions 106 of the legs 104 to return to their normal or non-parallel position, so that the distal portions overlap, after the staple 102 has been inserted into the body tissue 44.

Figure 11:
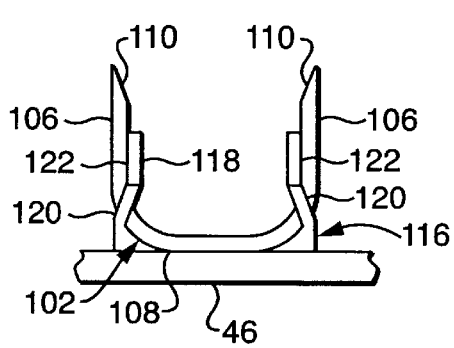
FIG. 11 is an enlarged side elevational view of a staple and a staple mount of the surgical stapler of FIG. 10.
Figure 12:
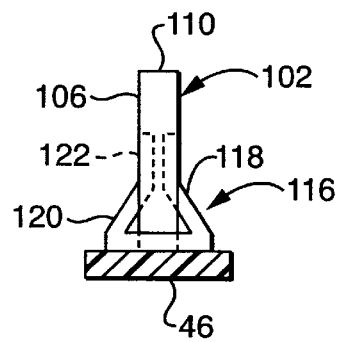
FIG. 12 is an end elevational view of the staple and the staple mount of the surgical stapler of FIG. 10.

As also shown in FIGS. 11 and 12, the staple mounts 116 each include two pairs of posts 118 holding the distal portions 106 of the legs 104 of the staples 102 parallel. Each post 118 includes a first portion 120 extending at an angle from the ejecting platform 46 to between the legs 104 of the staple 102, and a second portion 122 extending in the direction of staple ejection. The straight second portions 122 of the posts 118 support the distal portions 106 of the staples 102 in parallel positions, while the angled first portions 120 allow the base members 108 of the staples to pass between the posts 118, so that the staples 102 can be released by the mounts 116 after being inserted into the body tissue 44. The staple mounts 116 can take other, alternative forms, but in general must hold the distal portions 106 of the legs 104 of the staples 102 parallel prior to insertion into tissue, yet allow release of the staples 102 after insertion.

The upper jaw 114 of the stapler 100 includes recesses 124 for receiving and guiding the distal portions 106 of the legs 104 of the staples 102 into their overlapped positions. Although the particular embodiment of the stapler 100 of FIG. 10 is a linear type stapler having pivotally joined jaws, it should be understood that the unique features of the stapler can also be applied in other types of surgical staplers, such as a circular type surgical stapler.

Although preferred and other embodiments of the disclosure have been described herein, further embodiments may be perceived by those skilled in the art without departing from the spirit and scope of the disclosure as defined by the following claims.

I claim:

1. A surgical stapler comprising:
   a pair of jaws movable between open and closed positions;
   a handle and trigger assembly for controlling operation of the jaws;
   an elongated tubular structure connecting the handle and trigger assembly to the jaws;
   means for ejecting at least one staple from one of the jaws against the other of the jaws; and
   an anvil and a horn in the other of the jaws arranged to receive ends of the ejected staple such that the ends overlap between the anvil and the horn, the horn for melting and bonding at least a portion of the overlapping ends of the staple upon being energized by a predetermined form of energy, and wherein one of the anvil and the horn is movable from within the bonded staple to allow the jaws to be moved to an open position.

2. A surgical stapler according to claim 1, wherein the anvil is movable from within the bonded staple.

3. A surgical stapler according to claim 2, further including a rotatable shaft extending into the other of the jaws and operatively connected to the anvil such that rotation of the shaft slides the anvil from within the bonded staple.

4. A surgical stapler according to claim 1, wherein the predetermined form of energy comprises vibration energy.

5. A surgical stapler according to claim 1, further including at least one staple comprised of a thermoplastic material bondable by vibration energy.

6. A surgical stapler according to claim 5, wherein the staple is bio-absorbable.

7. A surgical stapler according to claim 1, wherein the stapler comprises a linear surgical stapler and the jaws are elongated and provide parallel rows of multiple bonded staples.

8. A surgical stapler according to claim 1, wherein the means for ejecting comprises:
   a platform for ejecting the staple upon being moved towards the other of the jaws;
   a cam for moving the platform towards the other of the jaws upon being rotated; and
   a bar for rotating the cam upon being linearly moved.

9. A method of stapling body tissue comprising:
   clamping body tissue between a pair of jaws;

ejecting at least one staple from one of the jaws, so that ends of the staple pass through the clamped tissue towards the other of the jaws;

receiving the ends of the ejected staple between an anvil and a horn in the other of the jaws such that the ends overlap;

energizing the horn with a predetermined form of energy so that the horn melts and bonds at least a portion of the overlapping ends of the staple; and moving one of the anvil and the horn from between the bonded staple and the body tissue to allow the jaws to be opened.

10. A method of stapling according to claim 9, wherein the anvil is moved from within the bonded staple.

11. A method of stapling according to claim 9, wherein the predetermined form of energy comprises vibration energy.

12. A method of stapling according to claim 9, wherein the at least one staple comprises a plurality of staples ejected in a predetermined pattern.

13. A method of stapling according to claim 9, wherein the at least one staple comprises a plurality of staples ejected in two pairs of linear, parallel, staggered rows.

14. A method of stapling according to claim 13, further comprising cutting the body tissue between the two pairs of linear, parallel, staggered rows of staples.

* * * * *